(12) United States Patent
Mendonsa et al.

(10) Patent No.: US 11,591,648 B2
(45) Date of Patent: Feb. 28, 2023

(54) NANOCHANNEL WITH MAGNETIC SENSOR FOR THE DETECTION OF MOLECULES

(71) Applicant: Seagate Technology LLC, Cupertino, CA (US)

(72) Inventors: Gemma Mendonsa, Minneapolis, MN (US); Riyan A. Mendonsa, Minneapolis, MN (US); Krishnan Subramanian, Shakopee, MN (US)

(73) Assignee: SEAGATE TECHNOLOGY LLC, Fremont, CA (US)

( * ) Notice: Subject to any disclaimer, the term of this patent is extended or adjusted under 35 U.S.C. 154(b) by 513 days.

(21) Appl. No.: 16/591,232

(22) Filed: Oct. 2, 2019

(65) Prior Publication Data

US 2021/0047682 A1  Feb. 18, 2021

Related U.S. Application Data

(60) Provisional application No. 62/886,211, filed on Aug. 13, 2019.

(51) Int. Cl.
| | |
|---|---|
| *C12Q 1/68* | (2018.01) |
| *C12Q 1/6869* | (2018.01) |
| *G01N 27/72* | (2006.01) |
| *G01N 33/487* | (2006.01) |

(52) U.S. Cl.
CPC ........... *C12Q 1/6869* (2013.01); *G01N 27/72* (2013.01); *G01N 33/48721* (2013.01)

(58) Field of Classification Search
CPC ....................................................... C12Q 1/68

USPC ................................................................ 435/6
See application file for complete search history.

(56) References Cited

U.S. PATENT DOCUMENTS

| | | | |
|---|---|---|---|
| 5,445,970 A | 8/1995 | Rohr | |
| 5,445,971 A | 8/1995 | Rohr | |
| 5,981,297 A | 11/1999 | Baselt | |
| 6,852,493 B2 | 2/2005 | Ramirez-Vick et al. | |
| 7,682,838 B2 | 3/2010 | Wang et al. | |
| 7,906,345 B2 * | 3/2011 | Wang ................ H01F 10/3254 436/526 |
| 8,053,244 B2 | 11/2011 | Ryan et al. | |
| 10,222,333 B2 | 3/2019 | Kotsbak | |
| 2018/0216169 A1 | 8/2018 | Wago et al. | |
| 2018/0216178 A1 | 8/2018 | Lee et al. | |
| 2018/0216179 A1 | 8/2018 | Yang et al. | |
| 2018/0216180 A1 | 8/2018 | Lee et al. | |
| 2018/0237850 A1 * | 8/2018 | Mandell ............ B01L 3/502761 |
| 2019/0390267 A1 * | 12/2019 | Asti ..................... C12Q 1/6876 |
| 2021/0130890 A1 * | 5/2021 | Robins ................... G16B 30/00 |
| 2021/0381997 A1 * | 12/2021 | Asti ..................... C12Q 1/6869 |

FOREIGN PATENT DOCUMENTS

WO    WO-2013056182 A1 *    4/2013    ....... G01N 33/48721

* cited by examiner

*Primary Examiner* — Aaron A Priest
(74) *Attorney, Agent, or Firm* — Holzer Patel Drennan

(57) ABSTRACT

Method of utilizing a nanochannel in combination with at least one magnetic sensor for detecting (e.g., identifying) molecules, cells, and other analytes. Particularly, the method includes bringing molecules, labeled with magnetic nanoparticles (MNPs), in close proximity to the magnetic sensor to identify the molecules via an output signal from the magnetic sensor. The method is particularly suited for identifying nucleotides of DNA and RNA strands.

10 Claims, 5 Drawing Sheets

NANOCHANNEL WITH MAGNETIC SENSOR FOR THE DETECTION OF MOLECULES

CROSS-REFERENCE

This application claims priority to U.S. Provisional application No. 62/886,211 filed Aug. 13, 2019, which is incorporated herein by reference for all purposes.

BACKGROUND

Numerous methods are known for molecule identification. These methods, however, have limitations in, e.g., sensitivity and run time. A higher sensitivity or signal/noise ratio would improve sequencing accuracy in long reads. Run times are long due to the need to pause after each base incorporation to obtain an optical signal and/or remove tags. Run times and sensitivity could be improved with the use of real-time sequencing using a non-optical system.

SUMMARY

This disclosure is directed to methods of utilizing a nanochannel in combination with at least one magnetic sensor for detecting (e.g., identifying) molecules, cells, and other analytes, including nucleotides from DNA and RNA. Particularly, the method includes bringing molecules, labeled with magnetic nanoparticles (MNPs), in close proximity to the magnetic sensor to identity the molecules via a signal change (e.g., a resistance) sensed by the magnetic sensor. The implementations described herein are methods of using MNPs to identify molecules as they pass through a nanochannel having at least one magnetic sensor incorporated therein or thereon.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. These and various other features and advantages will be apparent from a reading of the following detailed description.

BRIEF DESCRIPTION OF THE DRAWING

The described technology is best understood from the following Detailed Description describing various implementations read in connection with the accompanying drawing.

DETAILED DESCRIPTION

Figure 1:
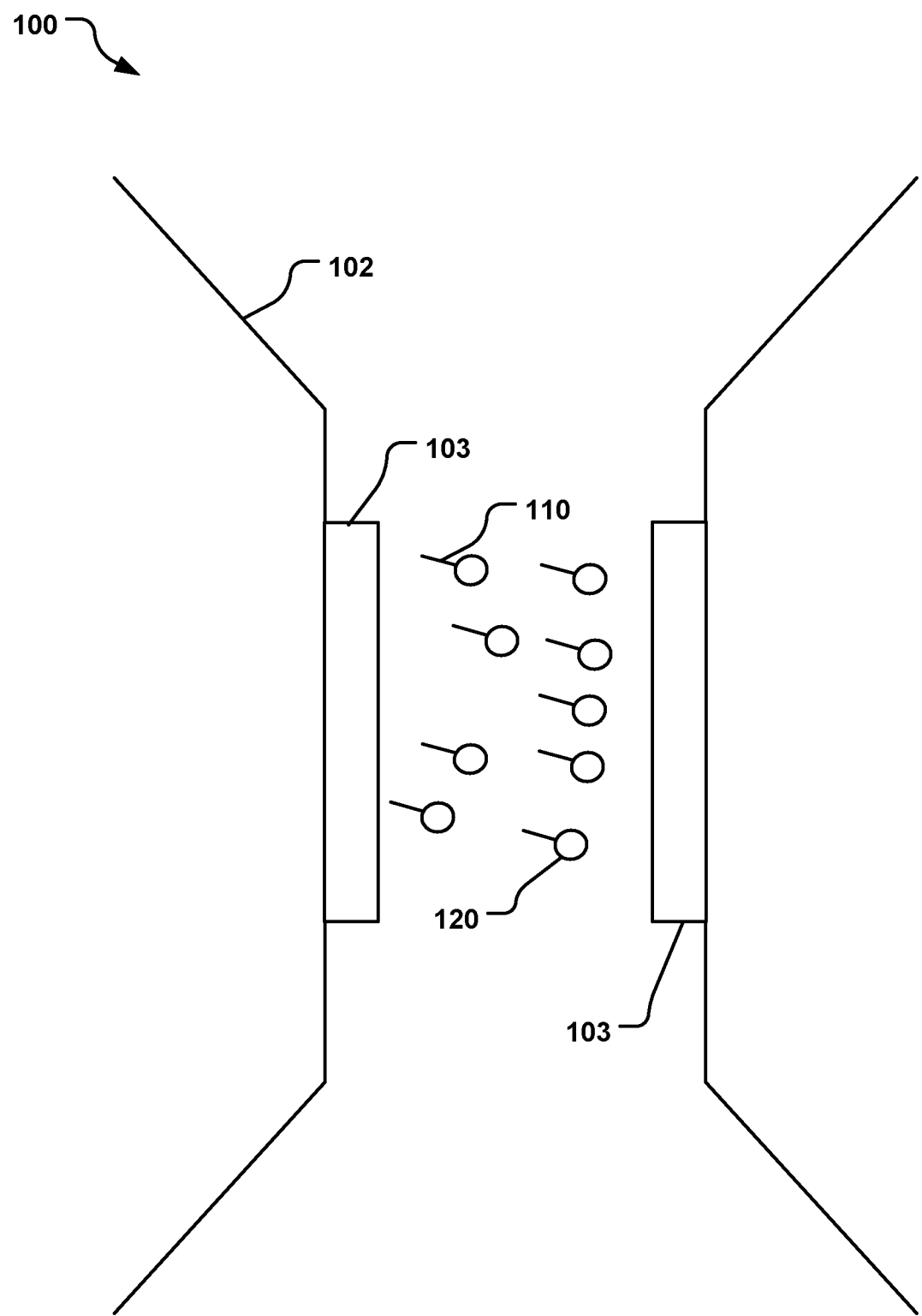
FIG. 1 is a schematic cross-sectional side view of a nanochannel having at least one magnetic sensor, the nanochannel being used to identify molecules labeled with magnetic nanoparticles.

As indicated above, in accordance with this disclosure, nanochannels and nanopores are used to identify biomolecules as they flow through the channel or nanopore. Many current nanochannel methodologies rely on direct electrical measurement of biomolecules as they pass through the channel. This process can be noisy, nonspecific, and have low sensitivity, providing poor accuracy in biomolecule identification. The methods of this disclosure utilize magnetic nanoparticles (MNPs) attached to the molecule to create a change in output signal of a magnetic sensor; this signal change (e.g., resistance) can be measured and then be used to count or identify the molecules. Such a method can be used for sequencing of nucleotides for DNA and RNA.

Current DNA sequencing methods face limitations in sequence read length, sensitivity, and run time. A higher sensitivity or signal/noise ratio would improve sequencing accuracy in long reads. Run times are long due to the need to pause after each base incorporation to obtain an optical signal and/or remove tags and could be improved with the use of real-time sequencing using a non-optical system. This disclosure provides DNA sequencing methods that overcome these undesired features. It should be noted that although the discussion here may use "DNA" when describing certain features, the methods of this disclosure are also applicable to RNA.

As indicated above, the present disclosure provides methods for real-time identification of molecules utilizing magnetic nanoparticles (MNP) and at least one magnetic sensor (e.g., a GMR, TMR, AMR, or Hall sensor). The methods include passing the molecules, having the MNPs attached thereto, through a nanochannel in close proximity to the magnetic sensor and then monitoring a change in an output signal (e.g., a resistance) due to the MNPs affecting the magnetic sensor.

The present disclosure also provides methods for real-time sequencing of nucleotides (DNA) utilizing magnetic nanoparticles (MNP) and a magnetic sensor (e.g., a GMR or TMR sensor). The methods include passing the nucleotides, having the MNPs attached thereto, through a nanochannel in close proximity to the magnetic sensor and then monitoring a change in an output signal (e.g., resistance) due to the MNPs affecting the magnetic sensor. In some implementations, an exonuclease at the nanochannel mouth is used to cleave the strand into individual MNP-labeled nucleotides. MNPs coming into close proximity to the magnetic sensor cause a dramatic change in signal the sensor, which can be measured so that the nucleotides can be identified.

Some of the methods described herein have improved sensitivity compared to optical and electrical detection and sequencing methods, including fluorescence, due to large resistance change caused by MNP-sensor interactions.

The description below provides numerous implementations.

One particular implementation described herein is a method of sequencing DNA or RNA. The method includes passing a DNA or RNA strand through a nanochannel having at least one magnetic sensor therein, the DNA or RNA strand comprising nucleotides A, D, G, T each labeled with a magnetic nanoparticle (MNP), each different type of nucleotide labeled with an MNP having a different magnetic moment, and identifying, in order, each MNP-labeled nucleotide of the strand by an output signal change from the magnetic sensor. Each type of nucleotide may be labeled with an MNP with a different size. In some methods, prior to identifying, the method includes cleaving the DNA or RNA strand with an exonuclease to form individual MNP-labeled nucleotides, and then identifying, in order, each individual MNP-labelled nucleotide of the strand by the output signal change from the magnetic sensor.

Another particular implementation described herein is a method of sequencing a DNA or RNA strand by providing a template strand, building a complementary strand from a plurality of individual nucleotides A, C, G, T, each type of nucleotide labeled with a magnetic nanoparticle (MNP) having a different magnetic moment, passing the complementary strand through a nanochannel having at least one magnetic sensor, and identifying, in order, each MNP-labeled nucleotide of the complementary strand by an output signal change from the magnetic sensor as the MNP-labeled nucleotides pass by the at least one magnetic sensor. Each type of nucleotide may be labeled with an MNP with a different size.

Yet another particular implementation described herein is a nanochannel having at least one magnetic sensor on a surface of the nanochannel, the nanochannel configured to receive MNP-labeled molecules therethrough and the magnetic sensor configured to detect the MNP passing therethrough.

Another particular implementation described herein is a method of sequencing DNA or RNA. The method includes forming a complementary strand by DNA or RNA polymerase from MNP-labeled nucleotides, passing the complementary strand through a nanochannel in close proximity to a magnetic sensor (e.g., for about 13.4 milliseconds) and obtaining a signal (e.g., a resistance) to identify the nucleotide. Different molecules (e.g., different nucleotides) have different sized MNP to provide a different signal changes in the magnetic sensor that can be readily identified.

Another particular implementation described herein is a method of identifying molecules by: providing a plurality of molecules, at least some labeled with a corresponding magnetic nanoparticle (MNP), different labeled molecules identified with a different sized MNP; passing the plurality of MNP-labeled-molecules through a nanochannel and exposing the plurality of MNP-labeled molecules to a magnetic sensor; and identifying each MNP-labeled molecule by a signal change from the magnetic sensor.

The method can be used to count the different labeled molecules and/or identify the different labeled molecules.

Yet another particular implementation described herein is a method of sequencing a DNA strand by: providing a template strand; building a complementary strand from a plurality of nucleotides each nucleotide labeled with a different sized magnetic nanoparticle (MNP); passing the complementary strand through a nanochannel having at least one magnetic sensor; and identifying, in order, each MNP-labeled nucleotide of the complementary strand by a signal change from the magnetic sensor. The complementary strand may be cleaved with an exonuclease to form individual MNP-labeled nucleotides that are identified by the at least one magnetic sensor.

The MNP-labeled nucleotides may be guided through the nanochannel by an applied electric or magnetic field.

In the following description, reference is made to the accompanying drawing that forms a part hereof and in which is shown by way of illustration at least one specific implementation. The following description provides additional specific implementations. It is to be understood that other implementations are contemplated and may be made without departing from the scope or spirit of the present disclosure. The following detailed description, therefore, is not to be taken in a limiting sense. While the present disclosure is not so limited, an appreciation of various aspects of the disclosure will be gained through a discussion of the examples provided below.

FIG. 1 illustrates a nanochannel sensing system 100 having a nanochannel 102 with at least one magnetic sensor 103 on a surface of the channel, the sensor 103 for detecting molecules 110 flowing through the channel 102. In the particular example illustrated, two sensors 103 are shown. The molecules 110 are labeled with an MNP 120; the molecules 110 may be, e.g., biomolecules, analytes, drugs, cells (e.g., prokaryotic and eukaryotic cells), etc.

As an MNP 120 comes into close proximity to the magnetic sensor 103, it causes a dramatic change in output from the sensor 103, which can be measured as an output signal. Depending on the magnetic moment of the MNP 120, the change in signal will differ quantitatively. The magnetic moment of the MNP 120 can differ due to, e.g., the size of the MNP 120, the shape of the MNP 120, the composition or material of the MNP 120, or by insulative coatings that may be present on the MNP 120. To distinguish, e.g., one type of molecule from another, two MNPs 120 having different magnetic moment can be used, resulting in a different output signal. The MNP 120 may be any magnetic material, e.g., ferromagnetic or paramagnetic.

Differently sized MNPs will cause different signal magnitudes, allowing specific detection of labeled molecules. Example sizes of MNPs include 10 nm, 20 nm, 30 nm, 40 nm, 50 nm, 100 nm, and any sizes therebetween, or smaller or bigger. Typically, the size (e.g., diameter) differentiation between multiple sizes of MNPs is at least 10 nm, in some implementations at least 15 nm and in other implementations at least 20 nm.

The magnetic sensor 103 can be any known magnetic sensor (e.g., GMR, TMR, AMR, Hall sensor) and can have any suitable configuration (e.g., CPP, CIP) with any number of ferromagnetic, antiferromagnetic, SAF, pinned, pinning, etc. layers. For GMR, TMR, and AMR sensors, a change in resistance is observed due to the MNP 120. For a Hall sensor, a change in output voltage is observed due to the MNP 120.

The nanochannel 102 has at least one sensor 103 present in the channel in or on a wall of the channel; in some implementations, multiple sensors 103 are present on opposite walls of the channel (e.g., two opposite walls for a square or rectangular channel), on all opposite walls (e.g., all four walls for a square or rectangular channel), on all walls (e.g., for a triangular, pentagonal, hexagonal, etc. channel). A circular channel may have any number of sensors, e.g., equally spaced around the circumference. The sensor(s) can be attached to the channel inner wall or may be formed integral with (e.g., fabricated as part of) the channel. In an alternate implementation, a sensor or sensors 103 may be positioned in the center of the channel (e.g., suspended in the channel between the walls) or otherwise displaced from the wall(s) of the channel.

The sensor or sensors 103 may be positioned anywhere along the length of the nanochannel 102. For example, the sensor(s) 104 may be at or proximate the mouth of the channel 102, in the longitudinal center, or at or proximate the end of the channel 102. In some situations, the sensor(s) are sufficiently large (area-wise) to occupy the entire length of the channel 102.

The surface of the channel 102 and/or the surface of the sensor or sensors 103 may be treated, coated or functionalized to attract, trap, interact with, repel, or otherwise affect the molecules 110 flowing through the channel 102.

As the MNP 120 passes through the nanochannel 102, in close proximity to the sensor 103, the MNP 120 causes a change in output signal in one or more of the sensors 103; for example, a change in resistance can be measured from some magnetic sensors. A large change in resistance in certain sensors (e.g., GMR, TMR sensors) caused by interaction with the MNP 120 produces a sensitive detection system with a large signal/noise ratio.

The size or dimension (of a cross-section of the channel, taken perpendicular to the channel length) is at least as big as the largest MNP 120 (i.e., the size of the channel is >1× of the largest MNP 120). Because of the need to have the MNP-labeled molecules pass in close proximity to the sensor 103 in order to register an output signal change, in some implementations, the channel diameter is no greater than 10× of the largest MNP 120. In some implementations, the channel diameter is 2×-10× of the largest MNP 120, in other implementations 2×-3×. The diameter of the channel may be constant along the length of the channel or may vary, e.g., taper.

The length of the nanochannel 102 is at least as long as the largest MNP 120 (i.e., the size of the channel is >1× of the largest MNP 120), although in many implementations, to get a solid change in the signal from the sensor(s) 104, the length of the channel 102 is at least 2× of the largest MNP 120, often at least 5×. As an example, the nanochannel 102 can have a length of 200-1000 nm, although in some implementations, nanochannels 102 as long as several micrometers can be used.

Although the sensing system 100 of FIG. 1 has been described as detecting molecules 110, the system 100 with a nanochannel 102 having at least one magnetic sensor 103 thereon is particularly well suited for identifying nucleotides and thus sequencing a DNA or RNA strand. The sequence of a template strand can be determined by identifying the nucleotides of a complementary strand.

Figure 2:
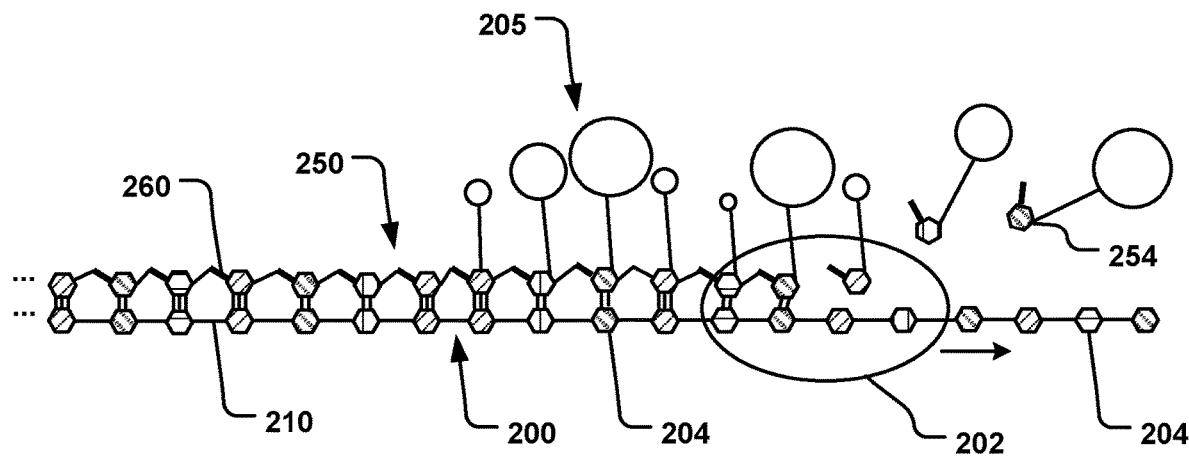
FIG. 2 shows an example DNA template strand and a complementary strand having nucleotides labeled with magnetic nanoparticles.

Turning to FIG. 2, a template strand 200 (composed of four nucleotides 204, particularly, A, C, G, T) is provided with an adapter 210, as is well known. An appropriate complementary primer 260 is annealed to the adapter 210 to initiate formation of a complementary strand 250. With a DNA polymerase 202, free or unattached nucleotides 254 assemble to form the remainder of the complementary strand 250, aligning with their complementary nucleotide 204 of the template strand 200. Such a process is well known.

In accordance with this disclosure, the nucleotides 254 are labeled with magnetic nanoparticle (MNPs) 205 having different magnetic moment, based on the identity of the nucleotide 254. The MNP 205 attaches to the nucleotide 254 at any location other that at a terminal phosphate of the nucleotide 254. Each of the four nucleotides 254 (A, C, G, T) is labeled with its own MNP 205, depending on its identity, thus each labeled nucleotide 254 has a different magnetic moment.

For nucleotides 254, when size (e.g., diameter) of the MNPs 205 is the distinguishing feature between the four different nucleotides 254, typically the size differentiation between the MNPs 205 is at least 10 nm, in some implementations at least 15 nm and in other implementations at least 20 nm. In one particular example, each of the four nucleotides 254 (A, C, G, T) is labeled with a differently-sized magnetic nanoparticle, such as 10 nm, 20 nm, 50 nm, 100 nm (not provided in any order). In another particular example, the four nucleotides 254 (A, C, G, T) are labeled with MNPs of 10 nm, 25 nm, 40 nm, 60 nm (not provided in any order). There is no requirement or recommendation regarding which nucleotide 254 (A, C, G, T) has the largest or the smallest sized MNP.

With the nucleotides 254 forming the complementary strand 250 labeled with MNPs 205, the nucleotides 254 can be identified by the output signal from a magnetic sensor.

Figure 3:
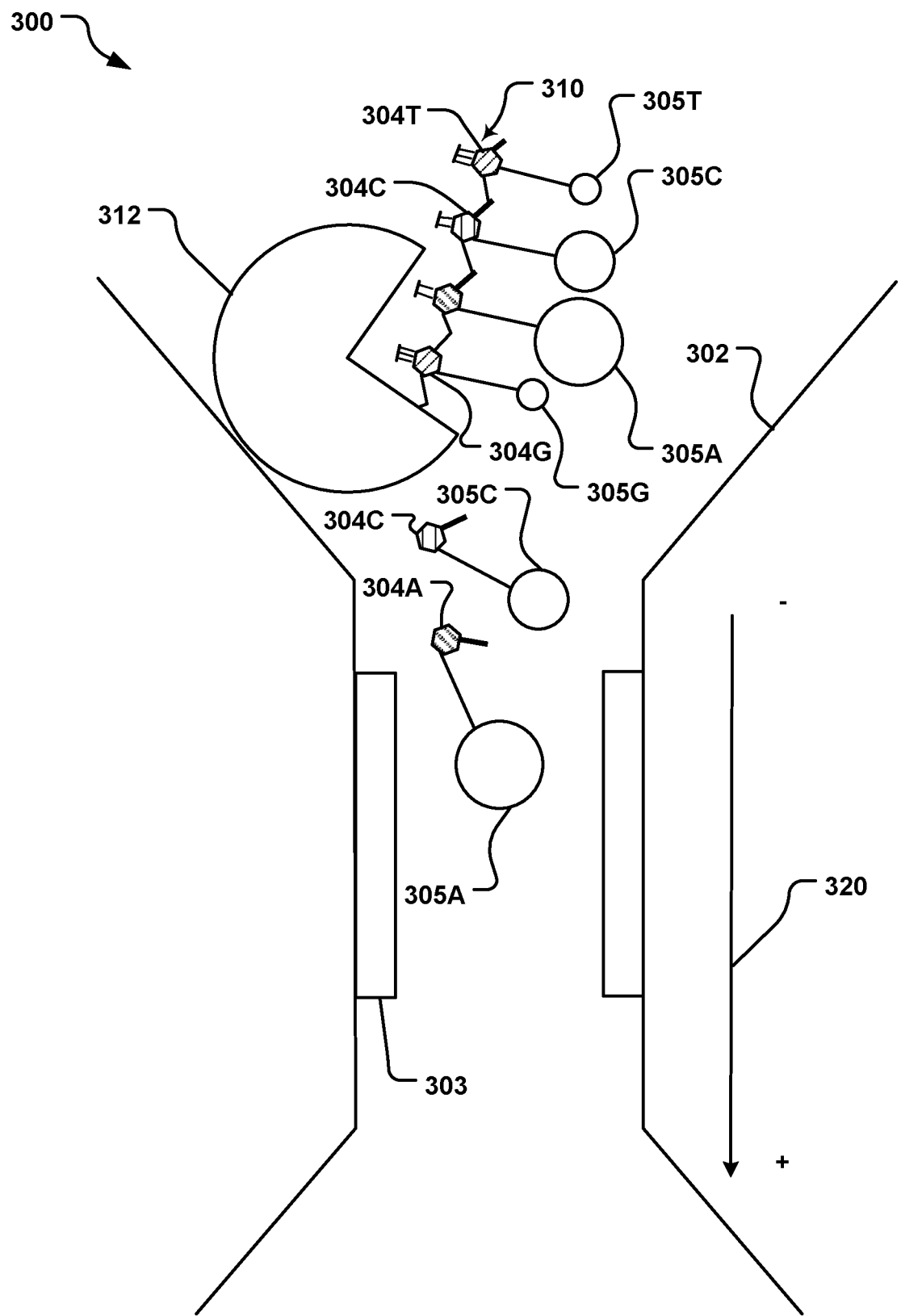
FIG. 3 is a schematic cross-sectional side view of a nanochannel having at least one magnetic sensor, the nanochannel being used to identify individual nucleotides labeled with magnetic nanoparticles.

FIG. 3 illustrates a nanochannel sensing system 300 having a nanochannel 302 with at least one magnetic sensor 303 on a surface of the channel, the sensor 303 for detecting nucleotides 304, labeled with an MNP 305, flowing through the channel 302. In the particular example illustrated, two sensors 303 are shown.

The size or dimension (of a cross-section of the channel 302, taken perpendicular to the channel length) is at least as big as the largest MNP 305 (i.e., the size of the channel is >1× of the largest MNP 305). Because of the need to have the MNP-labeled nucleotides pass in close proximity to the sensor 303 in order to register an output signal change, in some implementations, the channel diameter is no greater than 10× of the largest MNP 305. In some implementations, the channel diameter is 2×-10× of the largest MNP 305, in other implementations 2×-3×. The length of the nanochannel 302 is at least as long as the largest MNP 305 (i.e., the size of the channel is >1× of the largest MNP 305), although in many implementations, the length of the channel 302 is at least 2× of the largest MNP 350, often at least 5×.

The surface of the channel 302 and/or the surface of the sensor 303 may be treated, coated or functionalized to attract, trap, interact with, repel, or otherwise affect the nucleotides 304 and/or the MNP 305 flowing through the channel 302.

In the system 300, individual nucleotides 304, labeled with an MNP 305, pass through the channel 302 and past the sensors 303. The individual nucleotides 304, labeled with an MNP 305, are obtained from a complementary strand 310, prepared as described in respect to FIG. 2, above. The nucleotides 304 are labeled with MNPs 305 having different magnetic moment, based on the identity of the nucleotide 304. Each of the four nucleotides 304 (specifically, 304A, 304C, 304G, 304T) is labeled with its own MNP 305 (specifically, 305A, 305C, 305G, 305T), depending on its identity, thus each labeled nucleotide 305A, 305C, 305G, 305T has a different magnetic moment.

The complementary strand 310, composed of the MNP-labeled nucleotides, is digested by an exonuclease 312 immobilized at the entrance of the nanochannel 302. The MNP-labeled-nucleotides 304/305A, 304/305C, 304/305G, 304/305T are released from the complementary strand 310 by the exonuclease 312, one at a time, and then flow through the nanochannel 302 past the magnetic sensors 303. The exonuclease turnover rate can be less than 5 milliseconds (ms) per nucleotide, e.g., about 3.6 ms per nucleotide, although it may be faster or slower depending on the particular exonuclease 312.

An electrical or magnetic field 320 may be applied to guide the MNP-labeled-nucleotides 304/305A, 304/305C, 304/305G, 304/305T through the nanochannel 302. Such a field may be present within the nanochannel 302 or external to the nanochannel 302.

Figure 4:
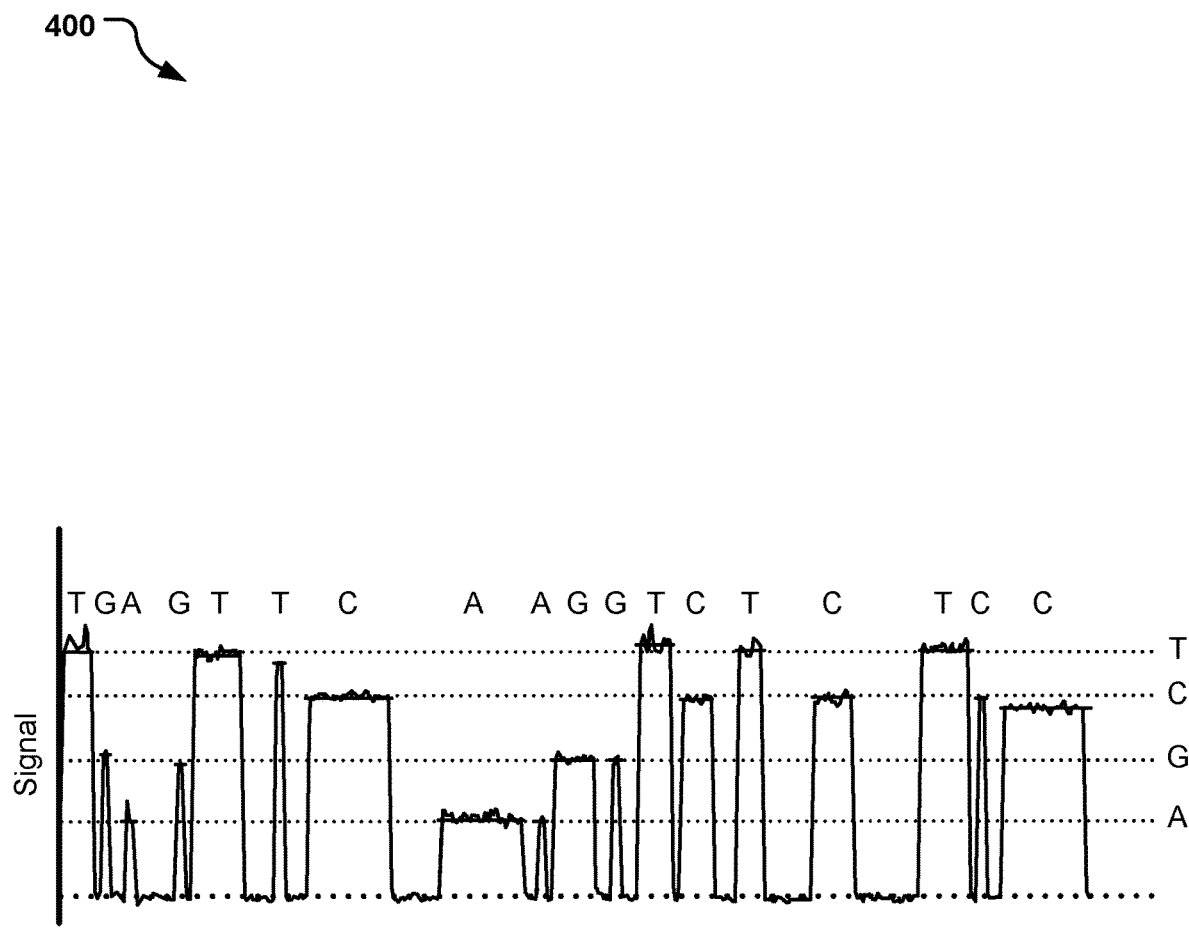
FIG. 4 is an example graphical representation of signal readout during a sequencing run of individual nucleotides.

One, some or all of the sensors 303 have a sequential change in signal as the MNP-labeled-nucleotides 304/305A, 304/305C, 304/305G, 304/305T pass by the sensor 303. The magnitude of the signal change corresponds to the size of the MNP 305 attached to the nucleotide 304, thus identifying the nucleotide 304 (e.g., as C, G, or T). A progression of labelled-nucleotides 304/305 will provide a sequence of signals, such as shown in FIG. 4 as graph 400.

A more detailed description of the steps in the proposed sequencing method, encompassing the discussion regarding FIG. 2 and FIG. 3, is provided below in Table 1.

TABLE 1

| | | |
|---|---|---|
| Step 1 | Prepare template strand | Ligate adapter sequence(s) onto the end(s) of template to be sequenced<br>Anneal complementary primer(s) to the adapter region(s) |
| Step 2 | Create MNP-labeled copy of template strand | Add DNA polymerase and MNP-labeled nucleotides to prepared template<br>Polymerase creates a complimentary copy of template with the MNP-labeled nucleotides |
| Step 3 | Attach exonuclease to nanochannel entrance | Exonuclease is attached to the entrance of detection nanochannel |
| Step 4 | Recruit copy strand and sequence | MNP-labeled copy strand added to nanochannel<br>Exonuclease digests copy strand one nucleotide at a time<br>MNPs detected as they are released from exonuclease into the detection nanochannel |
| Step 5 | Signal processing | Appropriate software used to sort signals, identify nucleotides |

It is noted that Step 2 and Step 3 may be done in either order, or, they may be performed simultaneously. In some implementations, Step 3 could be done simultaneously with Step 1. However, in all implementations, Step 1 is done prior to Step 2.

Figure 5:
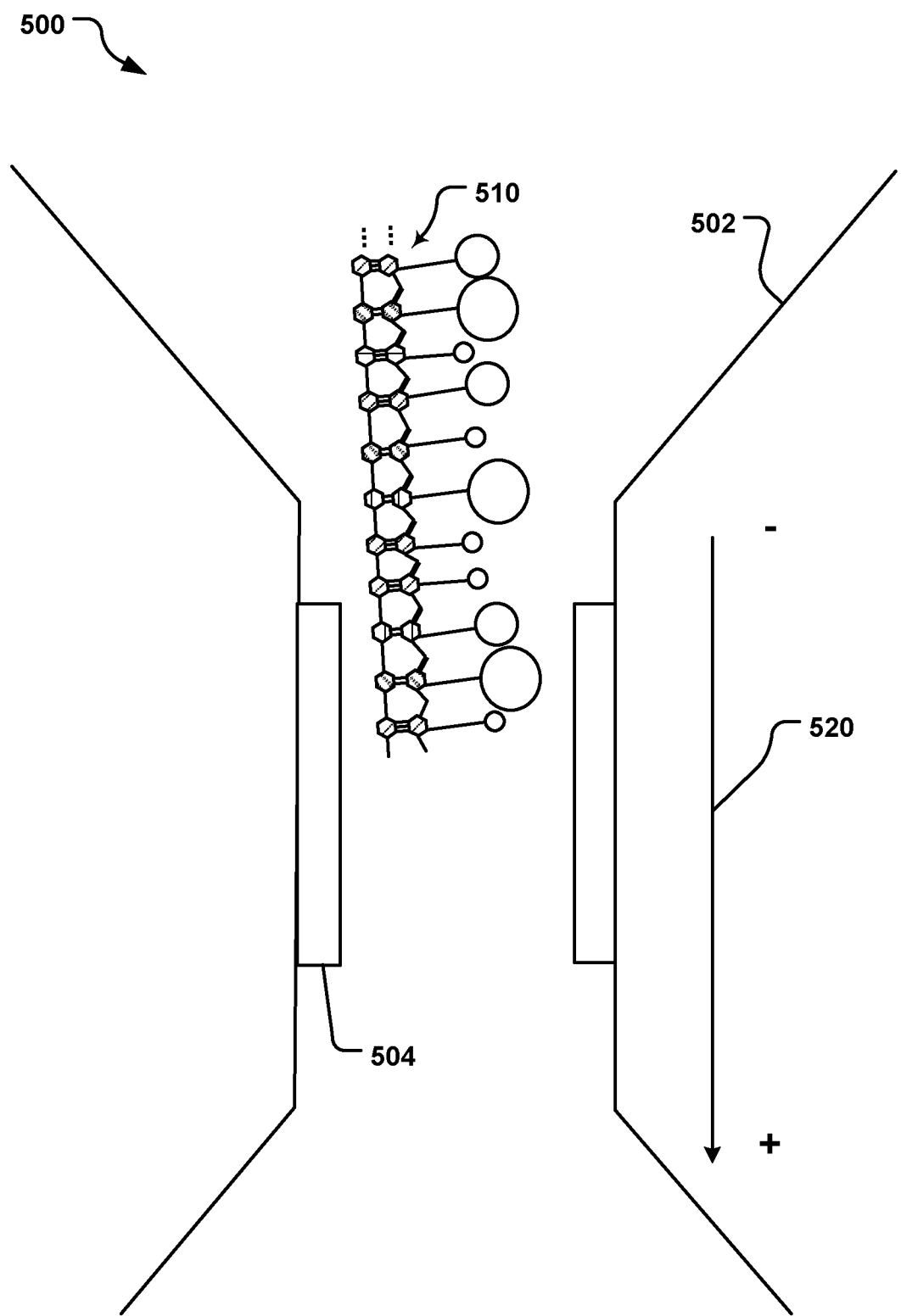
FIG. 5 is a schematic cross-sectional side view of a nanochannel having at least one magnetic sensor, the nanochannel being used to identify nucleotides labeled with magnetic nanoparticles.

In an alternate implementation, the MNP-labeled copy strand or complementary strand is not digested by the exonuclease but is instead fed intact through the nanochannel; see FIG. 5. In such an implementation, no exonuclease is present.

FIG. 5 illustrates a nanochannel sensing system 500 having a nanochannel 502 with at least one magnetic sensor 503 on a surface of the channel, the sensor 503 for detecting a strand 510 of nucleotides 504, labeled with an MNP 505, flowing through the channel 502. In the particular example illustrated, two sensors 503 are shown.

It is noted that the physical structure and configuration of the nanochannel 502 and the sensors 503 may be the same or different as that of the system 300 of FIG. 3. The length of the nanochannel 502, however, may be longer than described for the system 300. Because the strand 510 is composed of many nucleotides 504 labeled with an MNP 505, the length of the nanochannel 502 is at least as long as the largest MNP 505 (i.e., the size of the channel is >1× of the largest MNP 505), although in many implementations, the length of the channel 502 is at least 5× of the largest MNP 505, often at least 10×.

In the system 500, nucleotides 504, labeled with an MNP 305 and connected as a strand 510, pass through the channel 502 and past the sensors 503. The strand 510, having the nucleotides 504A, 504C, 504G, 504T labeled with a respective MNP 505A, 505C, 505G, 505T, can be prepared as described in respect to FIG. 2, above. The nucleotides 504 are labeled with MNPs 505 having different magnet moment, based on the identity of the nucleotide 504. Each of the four nucleotides 504 (specifically, 504A, 504C, 504G, 3504T) is labeled with its own MNP 505 (specifically, 505A, 505C, 505G, 505T), depending on its identity, thus each labeled nucleotide 505A, 505C, 505G, 3505T has a different magnet moment.

The MNP-labeled-nucleotides 504/505A, 504/505C, 504/505G, 504/505T flow through the nanochannel 502 past the magnetic sensors 503 as a single strand 510.

An electrical or magnetic field 520 may be applied to guide the strand 510 through the nanochannel 502.

One or both of the sensors 503 have a sequential change in signal as the MNP-labeled-nucleotides 504/505A, 504/505C, 504/505G, 504/505T pass by the sensors 503. The magnitude of the signal change corresponds to the size of the MNPs 305 attached to the nucleotides 504. A strand 510 will provide a sequence of signals, such as shown in FIG. 4 as graph 400, identifying the nucleotide 504 (e.g., as A, C, G, or T) in order.

A more detailed description of the steps of such a sequencing method, encompassing the discussion regarding FIG. 5, is provided below in Table 2.

TABLE 2

| | | |
|---|---|---|
| Step 1 | Prepare template strand | Ligate adapter sequence(s) onto the end(s) of template to be sequenced<br>Anneal complementary primer(s) to the adapter region(s) |
| Step 2 | Create MNP-labeled copy of template strand | Add DNA polymerase and MNP-labeled nucleotides to prepared template<br>Polymerase creates a copy of template with the MNP-labeled nucleotides |
| Step 3 | Recruit copy strand and sequence | MNP-labeled copy strand added to and passed through nanochannel<br>MNPs individually detected as the strand passes through the detection nanochannel |
| Step 4 | Signal processing | Software used to sort signals, identify nucleotides |

In any of the implementations described herein, one nanochannel may be present or multiple nanochannels may be present in a sensing system. Multiple nanochannels may be orderly arrayed for massively parallel detection and signal strength increase. Any nanochannels may be orderly arranged (e.g., in columns and/or rows) or may be randomly arranged. Multiple nanochannels may be situated in a plane (planar) or not.

The above specification and examples provide a complete description of the structure and use of exemplary implementations of the invention. The above description provides specific implementations. It is to be understood that other implementations are contemplated and may be made without departing from the scope or spirit of the present disclosure. The above detailed description, therefore, is not to be taken in a limiting sense. While the present disclosure is not so limited, an appreciation of various aspects of the disclosure will be gained through a discussion of the examples provided.

Unless otherwise indicated, all numbers expressing feature sizes, amounts, and physical properties are to be understood as being modified by the term "about," whether or not the term "about" is immediately present. Accordingly, unless indicated to the contrary, the numerical parameters set forth are approximations that can vary depending upon the desired properties sought to be obtained by those skilled in the art utilizing the teachings disclosed herein.

As used herein, the singular forms "a", "an", and "the" encompass implementations having plural referents, unless the content clearly dictates otherwise. As used in this specification and the appended claims, the term "or" is generally employed in its sense including "and/or" unless the content clearly dictates otherwise.

Spatially related terms, including but not limited to, "bottom," "lower", "top", "upper", "beneath", "below", "above", "on top", "on," etc., if used herein, are utilized for ease of description to describe spatial relationships of an element(s) to another. Such spatially related terms encompass different orientations of the device in addition to the particular orientations depicted in the figures and described herein. For example, if a structure depicted in the figures is turned over or flipped over, portions previously described as below or beneath other elements would then be above or over those other elements.

Since many implementations of the invention can be made without departing from the spirit and scope of the invention, the invention resides in the claims hereinafter appended. Furthermore, structural features of the different implementations may be combined in yet another implementation without departing from the recited claims.

What is claimed is:

1. A method of sequencing a DNA or RNA strand, comprising:
    passing a DNA or RNA strand through a nanochannel having at least one magnetic sensor therein, the DNA or RNA strand comprising nucleotides A, C, G, T each labeled with a magnetic nanoparticle (MNP), each different type of nucleotide labeled with an MNP having a different magnetic moment and a different size, a size of a MNP for one type of nucleotide at least 10 nm different than a size of a MNP for another type of nucleotide; and
    identifying, in order, each MNP-labeled nucleotide of the strand by an output signal change from the magnetic sensor.

2. The method of claim 1, further comprising:
    prior to identifying, cleaving the DNA or RNA strand with an exonuclease to form individual MNP-labeled nucleotides; and
    identifying, in order, each individual MNP-labeled nucleotide of the strand by the output signal change from the magnetic sensor.

3. The method of claim 1, wherein each nucleotide of the DNA or RNA strand is an MNP-labeled nucleotide.

4. The method of claim 1, wherein an output signal change from the magnetic sensor comprises an output resistance change.

5. The method of claim 1, wherein passing through the nanochannel includes utilizing a magnetic or electrical field.

6. A method of sequencing a DNA or RNA strand, comprising:
    providing a template strand;
    building a complementary strand from a plurality of individual nucleotides A, C, G, T, each type of nucleotide labeled with a magnetic nanoparticle (MNP) having a different magnetic moment and a different size, a size of a MNP for one type of nucleotide at least 10 nm different than a size of a MNP for another type of nucleotide;
    passing the complementary strand through a nanochannel having at least one magnetic sensor; and
    identifying, in order, each MNP-labeled nucleotide of the complementary strand by an output signal change from the magnetic sensor as the MNP-labeled nucleotides pass by the at least one magnetic sensor.

7. The method of claim 6, further comprising:
    prior to identifying, cleaving the complementary strand with an exonuclease to form individual MNP-labeled nucleotides; and
    identifying, in order, each individual MNP-labeled nucleotide of the strand by the output signal change from the magnetic sensor.

8. The method of claim 6, wherein each nucleotide of the complementary strand is an MNP-labeled nucleotide.

9. The method of claim 6, wherein an output signal change from the magnetic sensor comprises an output resistance change.

10. The method of claim 1, wherein passing through the nanochannel includes utilizing a magnetic or electrical field.

* * * * *